United States Patent
Tan et al.

(10) Patent No.: US 6,541,633 B1
(45) Date of Patent: Apr. 1, 2003

(54) BIS-(ORTHO-AMINOPHENOL)-CARBOXYLIC ACID AB$_2$ MONOMER

(75) Inventors: Loon-Seng Tan, Centerville, OH (US); Jong-Beom Baek, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/192,040

(22) Filed: Jul. 10, 2002

(51) Int. Cl.$^7$ .............................................. C07D 241/42
(52) U.S. Cl. ...................................................... 544/353
(58) Field of Search ......................................... 544/353

(56) References Cited

U.S. PATENT DOCUMENTS

| 4,125,725 A | 11/1978 | Duffy |
| 5,030,704 A | 7/1991 | Harris et al. |

OTHER PUBLICATIONS

Baek, J–B, Simko, S. R., Tan, L–S, Synthesis and Polymerization of a Bis(O–aminophenol)–Carboxylic Acid AB2 Monomer, *Polymer Preprints* 2001, 42(2), 502–503 (Published Aug. 12, 2001).

*Primary Examiner*—Emily Bernhardt
(74) *Attorney, Agent, or Firm*—Charles E. Bricker; Thomas L. Kundert

(57) ABSTRACT

An AB$_2$ monomer of the formula:

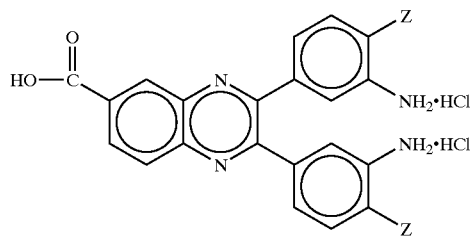

wherein Z is selected from the group consisting of —OH, —SH and —NH$_2$HCl, is useful for the preparation of hyperbranched polybenzoxazoles.

4 Claims, No Drawings

BIS-(ORTHO-AMINOPHENOL)-CARBOXYLIC ACID AB$_2$ MONOMER

RIGHTS OF THE GOVERNMENT

The invention described herein may be manufactured and used by or for the Government of the United States for all governmental purposes without the payment of any royalty.

BACKGROUND OF THE INVENTION

The present invention relates to a new quinoxaline-containing AB$_2$ monomer that is useful for the preparation of hyperbranched polybenzoxazoles.

Dendritic macromolecules such as dendrimers and hyperbranched polymers are a new class of highly branched polymers that have distinctly different properties from their linear analogs. Both dendrimers and hyperbranched polymers have much lower solution and melt viscosities than their linear analogs of similar molecular weights. They also have a large number of chain-ends whose collective influence dictates their overall physical and/or chemical behaviors. These features are attractive in terms of processability and offering flexibility in engineering required properties for specific applications. However, there is a practical advantage that hyperbranched polymers have over dendrimers at "raw material" level. Although dendrimers have precisely controlled structures (designated as generations), their preparations generally involve tedious, multi-step sequences that are impractical and costly in scale-up production. Synthesis of a hyperbranched polymer, on the other hand, is a one-pot process. Large quantities of hyperbranched polymers can be easily produced from AB$_x$(x≧2) monomers.

Because of their excellent thermal and mechanical properties, as well as their optical and electronic characteristics, aromatic, fused heterocyclic polymers such as polyquinoxalines and polybenzoxazoles continue to attract considerable attention. However, they have limited processability due to the nature of fused ring systems. Their insolubility and their softening temperatures are generally above their degradation temperatures. Chemical modification on the these materials, for example, by the use of solubilizing pendants or flexible units in the main chain, has been successful to improve their processability, allowing the optimization of their properties as a function of processability. Another viable approach to achieving this objective is to incorporate the elements of local rigidity and global randomness into the macromolecular architecture. Local rigidity provides the thermal, electronic and optical characteristics of the aromatic fused systems while global randomness frustrates entanglement of the polymer chains, leading to greater solubility. Dendritic structures clearly embody these qualities. However, as noted previously, hyperbranched structures have greater synthetic practicality.

Accordingly, it is an object of the present invention to provide novel quinoxaline-containing AB$_2$ monomers that are useful for the preparation of hyperbranched polybenzazoles.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided novel AB$_2$ monomers of the formula:

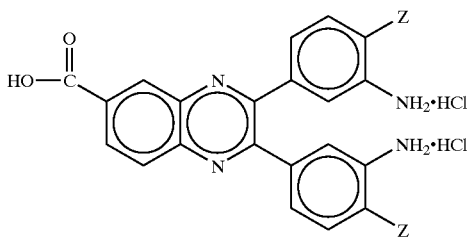

wherein Z is —OH, —SH or —NH$_2$.HCl.

DETAILED DESCRIPTION OF THE INVENTION

The AB$_2$ monomer, 2,3-bis(3-amino-4-hydroxyphenyl)quinoxaline-6-carboxylic acid dihydrochloride, is synthesized by condensing 3,4-diaminobenzoic acid and 4,4'-dimethoxybenzil to afford 2,3-bis(4-methoxyphenyl)quinoxaline-6-carboxylic acid, followed by demethylation in hydrobromic acid in acetic acid to form 2,3-bis(4-hydroxyphenyl)quinoxaline-6-carboxylic acid. The latter is then nitrated using nitric acid (70% conc.) in acetic acid at room temperature, yielding 2,3-bis(3-nitro-4-hydroxyphenyl)quinoxaline-6-carboxylic acid. The desired monomer is prepared by catalytic reduction in the presence of palladium catalyst in 10% hydrochloric acid.

The AB$_2$ monomer, 2,3-bis(3,4-diaminophenyl)quinoxaline-6-carboxylic acid dihydrochloride, is synthesized in a similar fashion, starting with 3,4-diaminobenzoic acid and 4,4'-dinitrobenzil. The condensation product is methylated to protect the carboxy group, reduced, acetylated to protect the amino groups, nitrated and reduced to provide the desired monomer.

The AB$_2$ monomer, 2,3-bis(3-amino-4-mercaptophenyl)quinoxaline-6-carboxylic acid dihydrochloride, is synthesized by condensing 3,4-diaminobenzoic acid and 3,3'-diaminobenzil. The condensation product is methylated to protect the carboxy group, halogenated, treated with thiocyanate and hydrolyzed to provide the desired monomer.

The AB$_2$ monomers can be self-polymerized to prepare hyperbranched polymers, as shown by the following equation:

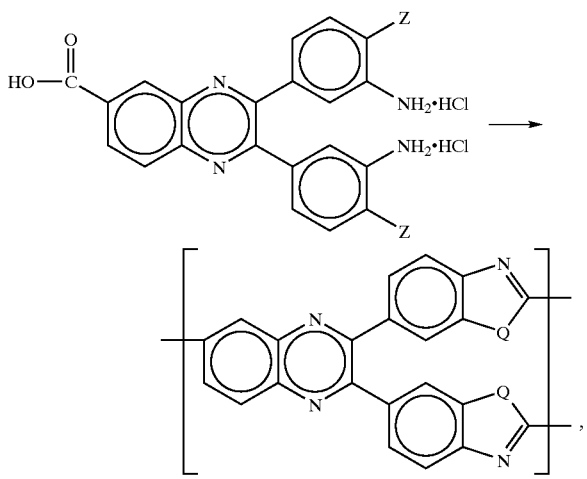

wherein Z is as described previously and Q is —O—, —S— or —NH—. Polymerization can be conducted in polyphosphoric acid (PPA) at a polymer concentration of about 6 weight percent at a temperature of up to about 130° C., or in the melt state.

The following examples illustrate the invention:

EXAMPLE 1

2,3-Diphenylquinoxaline-6-carboxylic Acid

Into a 500 mL three-necked, round-bottomed flask equipped with a magnetic stirrer, a condenser, and a nitrogen inlet, 3,4-diaminobenzoic acid (16.0 g, 105 mmol) was dissolved in deoxygenated acetic acid (250 mL). Benzil (21.0 g, 100 mmol) was then added in one portion. The mixture was heated under reflux for 12 h. During this time, off-white precipitate formed. After the reaction mixture had been allowed to cool to room temperature, the precipitate was collected to give 32.2 g (99% yield) of crude product, m.p. 290.5–292° C. Recrystallization of the crude product from DMF afforded 29.6 g (91% yield) of pink crystals, m.p. 291–292.5° C. Anal. Calcd. for $C_{24}H_{14}N_2O_2$: C, 77.29%; H, 4.32%; N, 8.57%; O, 9.80%. Found: C, 76.93%; H, 4.77%; N, 8.57%; O, 9.63%. FT-IR (KBr, $cm^{-1}$): 1690 (carbonyl). Mass spectrum (m/e): 326 ($M^+$, 100% relative abundance). $^1$H-NMR (DMSO-$d_6$, δ in ppm): 7.35–7.43 (m, 6H, Ar), 7.48–7.51 (d, 4H, Ar), 8.18–8.21 (d, 1H, Ar), 8.28–8.32 (dd, 1H, Ar), 8.65 (s, 1H, Ar), 13.51 COOH). $^{13}$C-NMR (DMSO-$d_6$, δ in ppm): 128.00, 128.20, 128.95, 129.04, 129.15, 129.41, 129.67, 130.65, 132.01, 138.31, 139.61, 142.23, 153.98, 154.61, 166.50.

EXAMPLE 2

2,3-bis(4-Methoxyphenyl)quinoxaline-6-carboxylic Acid

Into a 500 mL three-necked, round-bottomed flask equipped with a magnetic stirrer, a nitrogen inlet, and a condenser, 3,4-diaminobenzoic acid (14.21 g, 93.4 mmol) was dissolved in deoxygenated acetic acid (250 mL). 4,4'-Dimethoxybenzil (25,0 g, 92.5 mmol) was then added to the resulting brown and clear mixture at room temperature. The reaction mixture was heated under reflux with vigorous stirring for 8 h. After having been allowed to cool down to room temperature, the brown mixture was poured into distilled water. The resulting light brown precipitates were collected by suction filtration and then air-dried overnight. It was recrystallized from ethanol to give 34.8 g (97% yield) of yellow solid, m.p. 296–298° C. Anal. Calcd. for $C_{23}H_{18}N_2O_4$: C, 71.49%; H, 4.70%; N, 7.25%: Found: C, 71.51%; H, 4.55%; N, 7.11%. FT-IR (KBr, $cm^{-1}$): 1693 (carbonyl), 2838 (methyl). Mass spectrum (m/e): 386 ($M^+$, 100% relative abundance). $^1$H-NMR (DMSO-$d_6$, δ in ppm): 3.80 (s, 6H, OCH3), 6.92–6.96 (d, 4H, Ar), 7.44–7.48 (dd, 8.8.11–8.14 (d, 1H, Ar), 8.22–8.26 (dd, 1H, Ar), 8.58–8.59 (d, 1H, Ar), 13.49 (s, 1H, COOH). $^{13}$C-NMR (DMSO-$d_6$, δ in ppm): 55.12, 113.52, 128.90, 128.98, 130.48, 130.74, 131.06, 131.17, 131.49, 139.38, 142.08, 153.46, 154.06, 159.85, 159.97, 166.59.

EXAMPLE 3

2,3-bis(4-Hydroxyphenyl)quinoxaline-6-carboxylic Acid

Into a 1000 mL three-necked, round-bottomed flask equipped with a magnetic stirrer, a nitrogen inlet, and a condenser, 2,3-bis(4-methoxyphenyl)quinoxaline-6-carboxylic acid (34.7 g, 89.8 mmol) was dissolved in acetic acid (260 mL). Hydrobromic acid (48%, 500 mL) was then added to yellow clear mixture at room temperature. The reaction mixture was heated under reflux with vigorous stirring until the solution become homogeneous. It took about 6 h. After having been allowed to cool down to room temperature, the red-brown mixture was poured into distilled water. The resulting light brown precipitate was collected by suction filtration and dried under the reduced pressure to give 31.9 g (99% crude yield) of yellow solid, m.p. 315–317° C. (dec.). Anal. Calcd. for $C_{21}H_{14}N_2O_4$: C, 70.39%; H, 3.94%; N, 7.82%. Found: C, 66.70%; H, 3.98%; N, 7.20%. FT-IR (KBr, $cm^{-1}$): 1698 (carbonyl), 3396 (hydroxy). Mass spectrum (m/e): 358 ($M^+$, 100% relative abundance). $^1$H-NMR (DMSO-$d_6$, δ in ppm): 6.76–6.79 (d, 4H, Ar), 7.35–7.39 (d, 4H, Ar), 8.09–8.12 (d, 1H, Ar), 8.20–8.24 (d, 1H, Ar), 9.87–9.89 (d, 1H), OH), 13.50 (s, 1H, COOH). $^{13}$C-NMR (DMSO-$d_6$, δ in ppm): 114.93, 128.78, 129.21, 129.27, 130.39, 131.11, 131.23, 139.29, 142.06, 153.78, 154.38, 158.30, 158.44, 166.62.

EXAMPLE 4

2,3-bis(4-Hydroxy-3-nitrophenyl)6-quinoxaline-carboxylic Acid

Into a 500 mL three-necked, round- bottomed flask equipped with a magnetic stirrer, a nitrogen inlet, and a dropping funnel, 2,3-bis(4-hydroxyphenyl)quinoxaline-6-carboxylic acid (10.0 g, 27.9 mmol) was dissolved in acetic acid (200 mL). A solution of nitric acid (5 mL) in acetic acid (20 mL) was then added dropwise at room temperature for 20 min. The reaction mixture was stirred for additional 12 h at room temperature. The light orange mixture was poured into distilled water. The resulting yellow precipitates were collected by suction filtration and then air-dried overnight. Recrystallization of the crude product from acetic acid gave 12.2 g (97.5% yield) of bright yellow solid, m.p. 263–267.5° C. Anal. Calcd. for $C_{21}H_{12}N_4O_8$: C, 56.26%; H, 2.70%; N, 12.50%; O, 28.55%. Found: C, 55.99%; H, 3.06%; N, 12.14%; O, 27.68%. FT-IR (KBr, $cm^{-1}$): 1347, 1540 (Ar—$NO_2$), 1628 (carbonyl), 3421 (hydroxy). Mass spectrum (m/e): 448 ($M^+$, 100% relative abundance). $^1$H-NMR (DMSO-$d_6$, δ in ppm): 7.14–7.18 (dd, 2H, Ar), 7.61–7.65 (dd, 2H, Ar), 8.16–8.32 (m, 4H, Ar), 8.62–8.63 (d, 1H, Ar), 11.54 (s COOH). $^{13}$C-NMR (DMSO-$d_6$, δ in ppm): 118.87, 118.99, 126.82, 126.91, 128.84,128.90, 129.10, 129.59, 129.70, 130.48, 132.15, 136.18, 136.27, 136.56, 139.61, 142.23, 151.65, 152.25, 152.85, 152.94, 166.45.

EXAMPLE 5

2,3-bis(3-Amino-4-hydroxyphenyl)quinoxaline-6-carboxylic Acid Dihydrochloride Into a 500 mL high pressure bottle, 2,3-bis(4-hydroxy-3-nitrophenyl)quinoxaline-6-carboxylic acid (10.0 g, 22.3 mmol), palladium on activated carbon (10%, 0.5 g), and 10% hydrochloric acid solution (150 mL) were introduced. The bottle was placed on a Parr hydrogenator, purged with hydrogen several times, and then agitated at 60–65 psi for 24 h. After the resulting mixture had been filtered through Celite 545 to remove catalyst, the solvent was removed by vacuum distillation. The off-white residue was recrystallized from deoxygenated 20% hydrochloric acid to give 6.7 g (65% yield) of white crystals, m.p. 260° C. (dec.). Anal. Calcd. for $C_{21}H_{18}C_{12}N_4O_4$: C, 54.68%; H, 3.93%; Cl, 15.37%; N, 12.15%: Found: C, 48.80%; H, 4.75%; Cl, 20.79%; N, 10.91%. FT-IR (KBr, $cm^{-1}$): 1293 (Ar—$NH_2$), 1628 (carboxy), 3421 (Ar—OH). Mass spectrum (m/e): 344 ($M^+$—$CO_2$-2HCl 100% relative abundance). $^1$H-NMR (DMSO-$d_6$, δ in ppm): 7.13–7.16 (d, 2H, Ar), 7.30–7.31 (d, 2H, Ar), 7.78 (s, 2H, Ar), 8.17–8.21 (d, 1H, Ar), 8.27–8.28 (d, 2H, Ar), 8.6–8.61 (s, 1H, Ar), 10.11 (s, 4H, NH2), 11.47 (s, 2H, —OH). $^{13}$C-NMR (DMSO-$d_6$, δ in ppm): 115.79, 118.99, 125.61, 128.95, 129.07, 129.13, 129.33, 130.36, 130.80, 131.83, 139.41, 142.08, 152.13, 152.51, 153.08, 166.42.

EXAMPLE 6

Hyperbranched Poly(quinoxaline-benzoxazole) with o-Aminophenol Endgroups

Into a 100 mL resin flask equipped with a high torque mechanical stirrer, nitrogen inlet and outlet, and a pressure regulator, polyphosphoric acid (PPA, 30 g) was placed and stirred with dried nitrogen purging for 10 h. The monomer, 2,3-bis(3-amino-4-hydroxyphenyl)6-quinoxaline-carboxylic acid dihydrochloride (3.0 g, 6.5 mmol) was added and the resulting mixture was dehydrochlorinated under reduced pressure (1 mmHg) at 60° C. for 24 h and 100° C. for 6 h. Upon completion of the dehydrochlorination process, the mixture was gently heated to 130° C. When the oil-bath temperature was close to 130° C., the mixture was already too viscous to render further stirring ineffective. All the polymer dope was stuck onto the glass-rod stirrer and therefore, it was allowed to stand for 30 min at 130° C. At the end of the polymerization process, water was added into the flask and the resulting mixture was poured into a Waring blender. The polymeric product that initially formed bundles with residual PPA was chopped in the blender, collected by suction filtration, washed with diluted ammonium hydroxide and then repeatedly with large amounts of water. Finally, the hyperbranched polymer was dried under reduced pressure (1 mmHg) at 200° C. for 48 h. Its intrinsic viscosity was determined to be 1.04 dL/g (MSA, 30±0.1° C.). Anal. Calcd. for $C_{21}H_{12}N_4O_2$: C, 71.58%; H, 3.43%; N, 15.90%. Found: C, 69.56%; H, 3.68%; N, 15.17%. The homopolymer is designated PPQO-5 in Table I, below.

EXAMPLE 7

General Procedure for In-situ End-Capping Reaction (Method 1)

Into a 100 mL resin flask equipped with a high torque mechanical stirrer, a nitrogen inlet and outlet, and a pressure regulator, PPA (30 g) was placed and stirred with dried nitrogen purging for 10 h. The end-capper (90 mol % to $AB_2$ monomer) was added and heated to 100° C. until the mixture became homogeneous (2 h). The monomer, 2,3-Bis(3-amino-4-hydroxyphenyl)-quinoxaline-6-carboxylic acid dihydrochloride (3.0 g, 6.5 mmol) was added and the resulting mixture was dehydrochlorinated under reduced pressure (1 mmHg) at 60° C. for 24 h and 100° C. for 6 h. Upon completion of the dehydrochlorination, the mixture was gently heated to 130° C. for 24 h, and 160° C. for 24 h. The work up was followed as described in the previous procedure. The powdery product was finally dried under reduced pressure (1 mmHg) at 200° C. for 48 h. A range of intrinsic viscosities of 0.18–0.22 dL/g (MSA, 30±0.1° C.) were determined.

EXAMPLE 8

General Procedure for "Post-Polymerization" End-Capping (Method 2)

Into a 100 mL resin flask equipped with a high torque mechanical stirrer, a nitrogen inlet and outlet, and a pressure regulator, PPA (10 g) was placed and stirred with dried nitrogen purging for 10 h. The parent hyperbranched polymer from Example 6 (1.0 g, 2.8 mmol, [η]=1.04 dL/g) was added and stirred at 100° C. until the mixture become homogeneous. It usually took about 2–4 h. The corresponding endcapper (3-sulfobenzoic acid 5% excess amount), was then added at this temperature and stirred for 24 h, then at 160° C. for 48 h. The work up was followed as mentioned in the previous procedure. The powdery product finally dried under reduced pressure (1 mmHg) at 200° C. for 48 h. An intrinsic viscosity of 0.35 dL/g (MSA, 30±0.1° C.) was determined: Anal. Calcd. for $C_{28}H_{14}N_4O_5S$: C, 64.86%; H, 2.72%; N, 10.81%, 15.43%, 6.18%. Found: C, 63.36%; H, 3.43%; N, 10.42%, 13.97%. 5.33%.

EXAMPLE 9

Specific Endcapped Polymers

PPQO-6 was prepared by the reaction of 2,3-Bis(3-amino-4-hydroxyphenyl)quinoxaline-6-carboxylic acid dihydrochloride (Example 5), hereinafter referred to as $AB_2$ monomer, and monocarboxyl end-capper 2,3-diphenyl quinoxaline-6-carboxylic acid (method 1). PPQO-7 was prepared by the reaction of $AB_2$ monomer and 4-sulfobenzoic acid (method 1). PPQO-8 was prepared by the reaction of $AB_2$ monomer and 3-sulfobenzoic acid (method 2). Two attempts were made to prepare PPQO-9. The attempt to react PPQO-5 and 2-thiophenecarbonyl chloride (method 2) resulted in the formation of insoluble gel. Soluble PPQO-9 was prepared by the reaction of $AB_2$ monomer and 2-thiophenecarboxylic acid (method 1) at milder reaction conditions. PPQO-10 was prepared by the reaction of $AB_2$ monomer and 3,5-dihydroxybenzoic acid (method 1). The viscosity value and thermal properties of PPQO's 5–10 are given in Table I, below.

TABLE I

| | | | | $T_{5\%}$ (° C.)$^d$ | | | |
|---|---|---|---|---|---|---|---|
| PPQO- | Method | η* (dL/g)$^a$ | $T_g$ (° C.)$^b$ | In Air (Onset) | Char (%) at 900° C. | In Helium (Onset) | Char (%) at 900° C. |
| 5 | — | 1.04$^e$ | ND$^c$ | 421 (533) | 0.5 | 480 (619) | 50 |
| 6 | 1 | 0.19 | ND | — | — | — | — |
| 7 | 1 | 0.18 | ND | — | — | — | — |
| 8 | 2 | 0.35$^e$ | ND | 296$^f$ (510) | 2 | 288$^f$ (624) | 23 |
| 9 | 1 | 0.22 | ND | — | — | — | — |

TABLE I-continued

|  |  |  |  | $T_{5\%}$ (° C.)[d] | | | |
| --- | --- | --- | --- | --- | --- | --- | --- |
| PPQO- | Method | $\eta^*$ (dL/g)[a] | $T_g$ (° C.)[b] | In Air (Onset) | Char (%) at 900° C. | In Helium (Onset) | Char (%) at 900° C. |
| 9 | 2 | Insol. | ND | — | — | — | — |
| 10 | 1 | 0.23 | ND | 297 (486) | 3 | 301 (580) | 55 |

Note:
[a] Reduced viscosity determined with 0.5% solution in MSA at 30 ± 0.1° C.
[b] Glass transition temperature ($T_g$) determined by DSC with heating rate of 10° C./min
[c] ND = not detectable up to 450° C.
[d] The temperature at which 5% weight loss based on TGA thermogram obtained with a heating rate of 10° C./min
[e] Intrinsic viscosity determined by two points extrapolation to the origin in MSA at 30 ± 0.1° C.
[f] Desulfonylation temperature

Having thus described exemplary embodiments of the present invention, it should be noted by those skilled in the art that the disclosures herein are exemplary only that alternatives, adaptations and modifications may be made within the scope of the present invention.

We claim:

1. An AB$_2$ monomer of the formula:

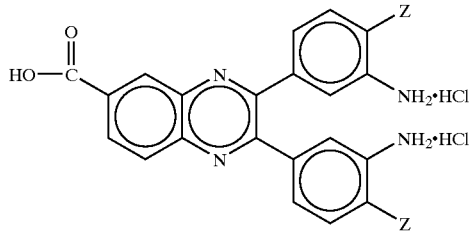

wherein Z is selected from the group consisting of —OH, —SH and —NH$_2$.HCl.

2. The monomer of claim 1 wherein Z is —OH.

3. The monomer of claim 1 wherein Z is —SH.

4. The monomer of claim 1 wherein Z is —NH$_2$.HCl.

* * * * *

UNITED STATES PATENT AND TRADEMARK OFFICE
CERTIFICATE OF CORRECTION

PATENT NO. : 6,541,633 B1  Page 1 of 1
DATED : April 1, 2003
INVENTOR(S) : Loon-Seng Tan et al.

It is certified that error appears in the above-identified patent and that said Letters Patent is hereby corrected as shown below:

<u>Column 3,</u>
Line 25, "13.51 COOH)" should read -- 13.51 (s, 1H, COOH) --.
Line 52, "(dd" should read -- (dd, 4H, Ar) --.

<u>Column 4,</u>
Line 15, "1H)," should read -- 1H --.
Line 63, "$C_{12}$" should read -- $Cl_2$ --.

<u>Column 7,</u>
Line 22, "and" should precede "that".

Signed and Sealed this

Twenty-eighth Day of October, 2003

JAMES E. ROGAN
*Director of the United States Patent and Trademark Office*